United States Patent
Sordillo-Gandy et al.

(12) 
(10) Patent No.: US 6,593,457 B1
(45) Date of Patent: Jul. 15, 2003

(54) LYMPHOCYTE-DERIVED ANTIMICROBIAL PROTEIN (LDAP) AND METHODS OF ISOLATING AND PRODUCING AND USING THE PROTEIN

(75) Inventors: Lorraine M. Sordillo-Gandy, Port Matida, PA (US); Kimberly A. Shafer-Weaver, Pleasant Gap, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/254,064

(22) PCT Filed: Aug. 27, 1997

(86) PCT No.: PCT/US97/14158

§ 371 (c)(1),
(2), (4) Date: Feb. 26, 1999

(87) PCT Pub. No.: WO98/08534

PCT Pub. Date: Mar. 5, 1998

Related U.S. Application Data (60) Provisional application No. 60/043,589, filed on Apr. 15, 1997, and provisional application No. 60/024,662, filed on Aug. 27, 1996.

(51) Int. Cl.[7] .................................................. C07K 1/00
(52) U.S. Cl. ...................... 530/350; 424/520; 424/534; 530/300
(58) Field of Search ................................ 424/93.2, 520, 424/534; 530/300, 350

(56) References Cited

PUBLICATIONS

Pettit et al. The development of site–specific drug delivery systems for protein and peptide pharmaceuticals. Trends in Biotechnology. vol. 16 (1998) pp. 343–349.*
Sigma Catalog (1993) p. 62 and 63.*
Gaddy et al. Cord blood CD16+CD56– cells with low lytic activity are possible precursers of mature nature killer cells. Cellular Immunology (1997) vol. 180, pp. 132–142.*
Lotzova et al. Human natural killer cell development from bone marrow progenitors: analysis of phenotype, cytotoxixity and growth. Natural Immunity (1993) vol. 12, pp. 209–217.*

Wyckoff III, JH, et al., Comparison of *Brucella abortus* antigen preparations for in vitro stimulation of immune bovine T–lymphocyte cell lines, *Veterinary Immunology and Immunopathology*, vol. 36, pp. 45–64 (1993).

Andersson, M., et al., NK–lysin, a novel effector peptide of cytotoxic T and NK cells. Structure and cDNA cloning of the porcine form, induction by interleukin 2, antibacterial and antitumour activity, *EMBO Journal*, vol. 14, No. 6, pp. 1615–1625 (1995).

Andersson, M., et al., NK–lysin, structure and function of a novel effector molecule of porcine T and NK cells, *Veterinary Immunology and Immunopathology*, vol. 54, pp. 123–126 (1996).

Pena, SV., et al., Processing subcellular localization, and function of 519 (Granulysin), a human late T cell activation molecule with homology to small, lytic granule proteins, *American Association of Immunologists*, vol. 158, pp. 2680–2688 (1997).

Garcia–Penarrubia, P. et al., Prostaglandins from human T suppressor/cytotoxic cells modulate natural killer antibacterial activity, *Journal of Experimental Medicine*, vol. 170, pp. 601–606 (1989).

Garcia–Penarrubia, P., et al., Antibacterial activity of human natural killer cells, *Journal of Experimental Medicine*, vol. 169, pp. 99–113 (1989).

Levitz, SM, et al., Direct antimicrobial activity of T cells, *Immunology Today*, vol. 16, pp. 387–391 (1995).

Quiroga, GH, et al., Cytologic responses of *Staphylococcus aureus*–infected mammary glands of heifers to interferon gamma and interleukin–2 treatment, *American Journal of Veterinary Research*, vol. 54, No. 11, pp. 1894–1900 (1993).

* cited by examiner

*Primary Examiner*—James Housel
*Assistant Examiner*—Ulrike Winkler
(74) *Attorney, Agent, or Firm*—Howard Eisenberg, Esq.

(57) ABSTRACT

A purified, soluble lymphocyte-derived antimicrobial protein that has a molecular weight of 16 kD on SDS-PAGE, is inactivated by heating at 56° C. for 30 minutes or by treatment with trypsin, is expressed by CD3–, CD2+ cytokine-stimulated cells', and is active against Gram positive or Gram-negative bacteria including *Staphylococcus aureus*.

14 Claims, 6 Drawing Sheets

SDS-PAGE OF PROTEIN FRACTIONS CONTAINING ACTIVITY
(SILVER STAINING)

| FRACTION | BACTERICIDAL ACTIVITY (%) | SPECIFIC ACTIVITY (ACTIVITY/μg PROTEIN) |
|---|---|---|
| CELL-FREE SUPERNATANT | 32.0 | 0.04 |
| DESALTED | 23.0 | 0.05 |
| FLOW THROUGH | 22.5 | 2.4 |
| DEAE FRACTION 1 | 27.0 | 5.7 |

FIG.1

SDS-PAGE OF PROTEIN FRACTIONS CONTAINING ACTIVITY
(COOMASSIE BLUE STAINING)

| FRACTION | BACTERICIDAL ACTIVITY (%) | SPECIFIC ACTIVITY (ACTIVITY/µg PROTEIN) |
|---|---|---|
| CELL-FREE SUPERNATANT | 32.0 | 0.04 |
| DESALTED | 23.0 | 0.05 |
| FLOW THROUGH | 22.5 | 2.4 |
| FRACTION 1 | 27.0 | 5.7 |

FLOW CYTOMETRIC PROFILE OF CD3 DEPLETED MONONUCLEAR CELLS STAINED WITH CD3 MONOCLONAL ANTIBODIES

FIG.3C FLOW CYTOMETRIC PROFILE OF CD3 DEPLETED MONONUCLEAR CELLS STAINED WITH CD2 MONOCLONAL ANTIBODIES

FIG. 4

LYMPHOCYTE-DERIVED ANTIMICROBIAL PROTEIN (LDAP) AND METHODS OF ISOLATING AND PRODUCING AND USING THE PROTEIN

CROSS-REFERENCE TO RELATED APPLICATIONS

Priority is hereby claimed from pending PCT application PCT/US97/14158, filed Aug. 27, 1997, which claimed the benefit of pending Provisional Application Nos. 60/024,662, filed Aug. 27, 1996; and 60/043,589, filed Apr. 15, 1997.

GOVERNMENT SPONSORSHIP

This invention was made with Government support under Grant No. 93-37204-9206 awarded by the U.S. Department of Agriculture. The Government has certain rights in the invention.

FIELD OF THE INVENTION

The present invention is drawn to a lymphocyte-derived antimicrobial protein (LDAP) which is useful in the prevention and treatment of bacterial, viral and fungal pathogen caused infection in food and companion animals. The present invention is further drawn to nucleic acids and nucleic acid analogues encoding the protein and methods of isolating the protein and expressing the protein as well as antibodies which recognize the protein.

BACKGROUND OF THE INVENTION

Bacterial, viral and fungal infections which effect food and companion animals are of clear and obvious concern throughout the world. Bacterial infections of concern include but are not limited to mastitis, including bovine mastitis, respiratory diseases, enteritis and septicemia. Viral diseases include, but are not limited to, leukosis virus, respiratory disease, rabies, rhinotracheitis, FeLV, distemper and warts. Fungal diseases include, but are not limited to, ringworm, histoplasmosis, systemic mycoses and dermatitis.

As one example of a bacterial infectious condition, bovine mastitis is the most important infectious disease affecting both the quality and quantity of milk produced in the world. Bovine mastitis affects every dairy farm and approximately 38% of all cows. Mastitis can cause destruction of milk-synthesizing tissues, resulting in decreased milk production and altered milk composition. Depending on the duration and severity of disease, the productive performance of infected dairy cattle may be diminished permanently. Consequently, mastitis continues to be the greatest deterrent to profitable dairy production. On average, losses associated with mastitis will cost American dairy producers about 2 billion dollars annually; worldwide losses are estimated at 25 billion dollars annually.

In spite of the severe economic impact of this disease on the dairy industry, the only widely accepted methods of mastitis control are based on post-milking teat disinfection and antibiotic therapy. These methods are not always cost effective due to milk loss during such treatments. There is also a growing concern over the presence of drug residues in the food supply out of a concern for public safety. It becomes obvious that an effective, safe, and economical preventative which reduces the dairy industry's dependence on chemo-therapeutics is a major unfilled need of the industry. Chemotherapeutics refers to the treatment of diseases with chemical agents.

SUMMARY OF THE INVENTION

The present invention is drawn to a purified soluble lymphocyte-derived antimicrobial protein (LDAP) having the following properties a molecular weight of 16 kD or 30–50 kD when associated with bovine serum albumin (BSA), a susceptibility to inactivation by heat treatment at 56° C. for 30 minutes or by trypsin, expression primarily by CD2+, CD3−, cytokine stimulated cells, and antimicrobial activity against both Gram-positive and Gram-negative bacteria; or a derivative of said protein which contains one or more conservative amino acid changes and which has antimicrobial activity against both Gram-negative and Gram-positive bacteria.

DETAILED DESCRIPTION

As indicated above, bacterial, fungal and viral infections which effect food and companion animals, are of clear and obvious concern throughout the world. For example, bovine mastitis continues to be the greatest deterrent to profitable dairy production. The incidence of mastitis increases when defense mechanisms of the mammary gland are impaired. Exposure to stressful stimuli or to some mastitis-causing pathogens can contribute to depressed immune functions within the mammary gland. If immunosuppressive changes in host immunity predispose animals to mastitis then methods of facilitating dysfunctional defense mechanisms in the mammary gland should increase disease resistance.

The periparturient period of dairy cattle is associated with diminished immune responses and increased incidence of mastitis (Nickerson, S. C. 1989. Immunological aspects of mammary involution. J. Dairy Sci. 72: 1665; Oliver, S. P. and L. M. Sordillo. 1988. Udder health in the periparturient period. J. Dairy Sci., 71: 2584). Diminished mammary gland immune function is due, in part, to alterations in neutrophil functions (Kehrli, M. E., B. J. Nonnecke, and J. A. Roth. 1989. Alterations in bovine neutrophil function during the periparturient period. Am. J. Vet. Res. 50: 207). Additionally, important lymphocyte effector functions such as proliferation as well as antibody and cytokine production have been shown to be reduced during this time (Harp, J. A. and B. J. Nonnecke. 1986. Regulation of mitogenic responses by bovine milk leukocytes. Vet. Immunol. Immunopathol. 11: 215; Kehrli, M. E., B. J. Nonnecke, and J. A. Roth. 1989. Alterations in bovine lymphocyte function during the periparturient period. Am. J. Vet. Res. 50:215; Nagahata, H., A., Ogawa, Y., Sanada, H., Noda, and S., Yamamoto. 1992. Peripartum changes in antibody producing capability of lymphocytes from dairy cows. Vet. Quarterly. 14:39; Sordillo, L. M., M. J. Redmond, M. Campos, L. Warren, and L. A. Babiuk. 1991. Cytokine activity in the bovine mammary gland secretions during the periparturient period. Can. J. Vet. Res. 55:298; Torre, P., P., Konur, and S. P. Oliver. 1992. Proliferative response of mammary gland mononuclear cells to recombinant bovine interleukin-2 (IL-2). Vet. Immunol. Immunopathol. 32:351). The role of nonspecific immune responses within the mammary gland has been well established. Conversely, considerably less is known about the protective role of resident lymphoid populations in the bovine mammary gland. Healthy mammary parenchymal tissue is infiltrated constitutively with lymphocytes, particularly during the periparturient period (Outteridge, P. M. and C. S. Lee. 1988. The defense mechanisms of the mammary gland of domestic ruminants. Prog. Vet. Microbiol. Immun. 4:165). Since lymphocytes are a predominant leukocyte type in healthy mammary tissue, these cells may act as an important first line of contact with invading microbial pathogens.

Protocols aimed at supporting important host defense mechanisms in companion or food-producing animals may be the most effective way of controlling bacterial, fungal and viral infections. Developing alternatives to chemotherapy for the prevention and control of pathogen caused infections is the purpose of this invention.

It has been shown that human lymphoid cells are capable of killing both Gram-positive and Gram-negative bacteria by an extracellular mechanism (Garcia-Penarrubia, P., F. T. Koster, R. O. Kelley, T. D. McDowell, and A. D. Bankhurst. 1989. Antibacterial activity of human natural killer cells. J. Exp. Med. 169:99). Lymphocytes isolated from the mammary glands of lactating dairy cattle have been shown to exhibit a novel antibacterial property. Upon stimulation with IL-2, these lymphocytes demonstrated increased ability to kill *Staphylococcus aureus* in a nonspecific manner (Sordillo, L. M., M. Campos, and L. A. Babiuk. 1991. Antibacterial activity of bovine mammary gland lymphocytes following treatment with IL-2. J. Dairy Sci. 74:3370).

The present invention is based on the observation that bovine mammary gland tissues are infiltrated heavily with lymphoid cells and that stimulation of these cells with cytokines, such as IL-2, results in the generation of lymphocytes with the ability to kill bacterial targets in vitro. It is believed that this non-specific defense mechanism which is situated at strategic anatomical sites in the mammary gland that would allow prompt response to invading bacterial pathogens and contribute significantly to host defense against bacterial infections.

The present invention is drawn to a soluble factor which mediates this unique antibacterial effector function of lymphocytes.

More specifically the present invention is drawn to a soluble antimicrobial protein, produced primarily by $CD2^{30}$ $CD3^{31}$ lymphocytes, having a molecular weight of approximately 30–50 kD when complexed with BSA and a purified molecular weight of approximately 16 kD, as determined by SDS-PAGE and having bactericidal activity against Gram-negative and Gram-positive pathogens which cause bacterial infections without adversely affecting host cells. This protein has been designated as LDAP and such designation in the present application will be used to refer to the protein.

The LDAP protein of the present invention has been shown to be active against both Gram-negative and Gram-positive bacteria, including *Staphylococcus aureus, Streptococcus uberis* and *Escherichia coil* (Table 7).

The presently claimed protein may be isolated from immune or non-immune lymphocytes which have been activated with cytokines, such IL-2 or interferon, or bacteria. The antimicrobial activity of the protein results in non-Major Histocompatibility Complex (MHC) restricted lysis of the pathogen.

The present invention encompasses both LDAP isolated from natural sources and recombinant LDAP protein. Recombinant LDAP may be expressed using conventional recombinant techniques and expression systems such as those presented in Sambrook et al. Molecular Cloning, A Laboratory Manual, Cold Spring Harbor Press.

It is contemplated that with such expression systems, nucleic acid and nucleic acid analogues, including single and double DNA and RNA, encoding LDAP may be, for example, inserted into a suitable plasmid vector. The nucleic acid and nucleic acid analogues encoding LDAP may be obtained from either a lymphocyte cDNA library or synthetically synthesized. The vector containing the nucleic acid and nucleic acid analogues encoding LDAP may then be expressed in suitable host cells. Suitable host cells include bacterial expression systems such as *E. Coli*, or eurkaryotic expression systems such as baculovirus systems, mammalian transformed cells and fungal systems such as yeast.

The present invention is further drawn to nucleic acid and nucleic acid analogues sequences, including DNA and RNA, encoding LDAP, as well as nucleic acid and nucleic acid analogue sequences which hybridize under stringent conditions to a complementary strand of a nucleic acid and nucleic acid analogue sequence encoding LDAP. Stringent hybrization conditions may be as presented in Sambrook et al. Molecular Cloning, A Laboratory Manual, Cold Spring Harbor Press.

Nucleic acid analogues encompass any naturally occurring nucleic acid which has been modified or derivatized. Included as nucleic acid analogues are substituted nucleotide units. Such substituted nucleotide units include nucleotide units which confer resistance to nucleases and which are also compatible with polymerase chain reaction amplification. Examples of nucleic acid analogues include substituted pyrimidines, such as 2'fluoro-pyrimidines including 2'-fluoro-2'deoxycytidine or 2'-fluoro-2'-deoxyuridine residues. The substituted pyrimidines may also comprise 2'-amino-pyrimidine such as 2'-amino-2'-deoxycytidine or 2'-amino-2'deoxyuridine residues. The nucleotide units may also comprise substituted purines such as 2'-fluoro-purine including 2'-fluoro-2'-deoxyadenine or 2'-fluoro-2'deoxyguanidine residues. Also included are substituted purines comprising 2'-amino-purine and including 2'-amino-2'deoxyadenine or 2'amino-2'-deoxyguanidine residues. Nucleic acid analogues further encompass nucleic acids which have been modified to contain a chemical, fluorescent or radioactive marker.

Also encompassed by the present invention are LDAP proteins containing one or more conservative amino acid changes from the native protein. It is well understood in the art that conservative changes may be made to a protein while retaining function of the protein. Such conservative amino acid changes are those wherein amino acid substitutions are made which maintain charge identity of amino acid residues and steric configurations of amino acids. For example, acidic amino acids may be substituted for other acidic amino acids and one sterically bulky amino acid may be substituted for another. Conservative amino acid changes also include the deletion or addition of one or more amino acids, particularly from the amino or carboxy terminal end of the protein such that the antimicrobial activity of the protein is retained.

Given the small size of LDAP, derivatives which encompass conservative amino acid changes may be made using conventional techniques as presented in Sambrook et al. Molecular Cloning, A Laboratory Manual, Cold Spring Harbor Press. Such derivatives may be readily assayed for activity as described in the Examples, below. For example, it will be readily apparent to one practicing the present invention to determine portions of LDAP protein which may be deleted from the amino or carboxy terminal end of the protein while retaining activity. Such proteins which contain conservative amino acid changes are considered to be encompassed by the present invention.

It is contemplated based on accepted knowledge regarding the biochemistry of proteins that significant portions of a protein's amino acid sequence may be altered either synthetically or as naturally occurs between different species, wherein the protein maintains its biological activity. As such, the present invention further encompasses a functionally active protein which has at least 60% homology, preferably at least 80% homology, more preferably at least 95% homology to LDAP isolated from bovine peripheral blood lymphocytes.

The present invention is further drawn to pharmaceutical compositions containing LDAP. Such pharmaceutical compositions may be used in both the prophylaxis and treatment of pathogen caused infections in food and companion animals. Administration of LDAP to other food and companion animals during periods of diminished immune response will help prevent bacterially induced infectious diseases. For example, the periparturient period of dairy cattle is associated with diminished immune responses and an increased incidence of mastitis. Administration of exogenous LDAP to the dairy cattle during the periparturient period with help prevent the occurrence of mastitis.

LDAP protein is also useful in the treatment of pathogen based infections in food and companion animals. LDAP may be administered to an animal as a antimicrobial therapeutic.

Pharmaceutical compositions containing LDAP protein are administrable in the form of tablets, pills, powder mixtures, capsules, dispersions, solutions, suppositories, transdermal patches, emulsions, micelles, gels, liposomes injectables and in other suitable forms. The pharmaceutical compositions may be administered orally, parentally (including subcutaneous intradermal, intramuscular and intravenous administrations), topically or rectally. The most suitable route for administration will depend on, the identity and severity of the pathogen caused disease being treated or prevented. The pharmaceutical preparation which contains the compound is conveniently admixed with a nontoxic pharmaceutical organic or inorganic carrier, usually about 0.01 mg up to 20 mg, or higher per dosage unit, preferably 0.01 mg to 2 mg.

Typical pharmaceutically acceptable carriers are, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid dimethylsulfoxide and other conventionally employed acceptable carriers in which proteins are stable. The pharmaceutical preparation may also contain nontoxic auxiliary substances such as emulsifying, preserving, wetting agents, excipients and the like as for example, sorbitan monolaurate, triethanolamine oleate, polyoxyethylene monostearate, glyceryl tripalmitate, dioctyl sodium sulfosuccinate and the like.

Of particular interest are injectable forms of pharmaceutical compositions containing LDAP. LDAP may be freeze dried and, if desired, combined with other pharmaceutically acceptable excipients to prepare formulations suitable for subcutaneous parenteral, intravenous, or intramuscular injectable administration. For such administration, the formulation can be reconstituted in water (normal, saline) or a mixture of water and an organic solvent, such as propylene glycol, ethanol, and the like. Also of interest are topical pharmaceutical formulations containing LDAP. Topical formulations will be useful in the application of LDAP to localized infections, such as dermatitis. Such topical formulations include teat dips and the like. Topical formulations may further include antiseptics, analgesics, moisturizers and the like.

The dose administered may be given as a single dose, multiple doses or a daily dose in an immediate acting form or sustained release formulation using a biodegradable polymer, for example, and will, of course, vary with the chosen route of administration, size of the animal to be administered and the condition of the animal. A typical dose will be in the range of 10 $\mu$g/kg body weight to 250 mg/kg body weight, preferably 10 $\mu$g/kg to 25 mg/kg more preferably 10 $\mu$g/kg to 2 mg/kg.

The pharmaceutical compositions of the present invention may also contain additional active components such as natural or synthetic antibiotics, antipyretics, and analgesics.

The present invention is further drawn to antibodies raised against the LDAP protein. Such antibodies may be either polyclonal or monoclonal and may be generated by conventional techniques such as those in Sambrook et al. Molecular Cloning, A Laboratory Manual, Cold Spring Harbor Press. Antibodies raised against LDAP may be useful in the isolation of the protein and in diagnostic procedures in detecting the presence of the protein.

The present invention is further drawn to methods of treatment with LDAP.

In conjunction with the methods of treatment using LDAP protein the present invention is further drawn to a kit containing LDAP and a suitable carrier.

The components of the present invention may be packaged as a kit. Uses of the kit may be for the prevention or treatment of pathogen caused infections in food and companion animals with LDAP. Alternatively, the kit may be for diagnostic purposes with antibodies which recognize LDAP. Each component of the kit(s) may be individually packaged in its own suitable container. The individual containers may also be labelled in a manner which identifies the contents. Moreover, the individually packaged components may be placed in a larger container capable of holding all desired components. Associated with the kit may be instructions which explain how to use the kit. These instructions may be written on or attached to the kit.

EXAMPLES OF THE INVENTION

Example 1

Isolation of Lymphoid Cells

Effector cells were obtained by isolation of mononuclear leukocyte populations from bovine mammary gland tissue and peripheral bovine blood. Mononuclear cells were obtained by centrifugation through density gradients (approximately 1.077 g/ml). Monocytes were removed from the isolated mononuclear cells by adherence to plastic to obtain enriched lymphocytes.

The mononuclear leukocyte populations were cultured for 48 hours in IL-2. Functional activity was evaluated by assays for bactericidal activity and cytotoxicity and the cell phenotypes were evaluated by flow cytometry.

Assay of Bacterial and Cytotoxic Activity of IL-2 Stimulated Mammary Gland Lymphocytes Bacterial and cytotoxic activity of mammary gland lymphocytes is presented in Table 1.

TABLE 1

BACTERIAL AND CYTOTOXIC ACTIVITY OF MAMMARY GLAND LYMPHOCYTES

| Treatment | % Bacterial Activity | % Cytotoxic Activity |
|---|---|---|
| Control | 11.71 | 1.30 |
| IL-2 | 37.59* | 26.60** |

Bactericidal activity against *S. aureus*.
Cytotoxic activity against K562 target cells.

Antimicrobial activity was measured against *S. aureus* and cytotoxic activity was measured against K562 target cells. The data clearly show increased bactericidal and cytotoxic activity with IL-2 stimulated cells.

Using magnetic bead separation various populations of lymphoid cells were prepared. To isolate the desired cell populations isolated lymphoid cells were incubated with monoclonal antibodies to a desired cell population and antibody coated magnetic beads which recognized the monoclonal antibody bound cells. Pure positive populations and depleted negative populations of a specific cell type were then extracted using a magnetic field.

The isolated effector cells were then incubated with IL-2 for 48 hours and evaluated for functional capacity by bactericidal assays and for phenotype by flow cytometry. The bactericidal activity of various cell populations of effector cells is shown in Table 2. From these studies it was shown that cells which are CD2+ and CD3− demonstrate the highest levels of bactericidal activity.

TABLE 2

BACTERICIDAL ACTIVITY EXPRESSED BY PURIFIED AND DEPLETED PERIPHERAL BLOOD LYMPHOCYTES

| | Bactericidal Activity | |
|---|---|---|
| Cell Populations[1] | Spontaneous[3] | LAK[4] |
| | ----- (% Killing) ----- | |
| CD2+ | 12.3 ± 3.5$^a$ | 37.3 ± 3.5$^{a***}$ |
| CD2− | 1.9 ± 3.5$^b$ | 2.1 ± 3.3$^b$ |
| CD4+ | 10.0 ± 3.5$^b$ | 17.6 ± 3.5$^b$ |
| CD4− | 25.6 ± 3.5$^a$ | 32.5 ± 3.5$^a$ |
| CD8+ | 9.0 ± 2.3$^b$ | 9.7 ± 2.3$^b$ |
| CD8− | 19.9 ± 2.3$^a$ | 32.7 ± 2.3$^{a***}$ |
| WC1+ | 1.0 ± 3.3$^b$ | 5.7 ± 3.3$^b$ |
| WC1− | 11.3 ± 4.0$^a$ | 23.0 ± 4.0$^{a*}$ |
| CD3+ | 4.7 ± 3.0$^b$ | 9.3 ± 3.0$^b$ |
| CD3− | 16.4 ± 3.0$^a$ | 25.6 ± 3.0$^{a*}$ |
| B+ | 6.0 ± 4.0 | 9.6 ± 4.0$^b$ |
| B− | 13.0 ± 4.0 | 25.4 ± 4.0$^{a*}$ |

[1]Cells with the "−" superscript are depleted of that specific cell subset. Cells with the "+" superscript are pure phenotype cultures (≧97%).
[2]Cultures were incubated for 30 min with bacterial-effector cell contact. Bactericidal activity is expressed as least square means ± standard error.
[3]Effector cells were incubated for 48 h in the absence of cytokine stimulation.
[4]Effector cells were incubated for 48 h with recombinant human interleukin-2.
$^{ab}$Significantly differ with respect to cell culture within a stimulation group ($P < 0.05$).
*Significantly differ with respect to stimulation within a culture group ($P < 0.05$).
***Significantly differ with respect to stimulation within a culture group ($P < 0.01$).

Figure 3A:
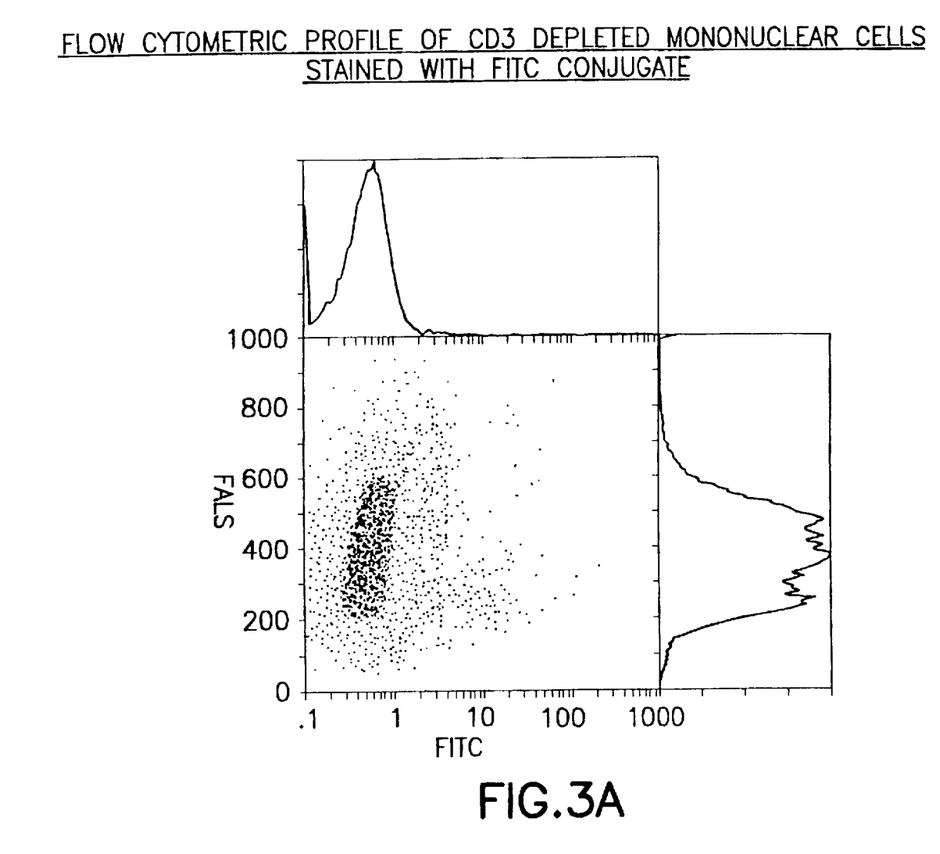
FIG. 3A shows control labelling of CD3 depleted cells with a FITC-conjugate secondary antibody.
Figure 3B:
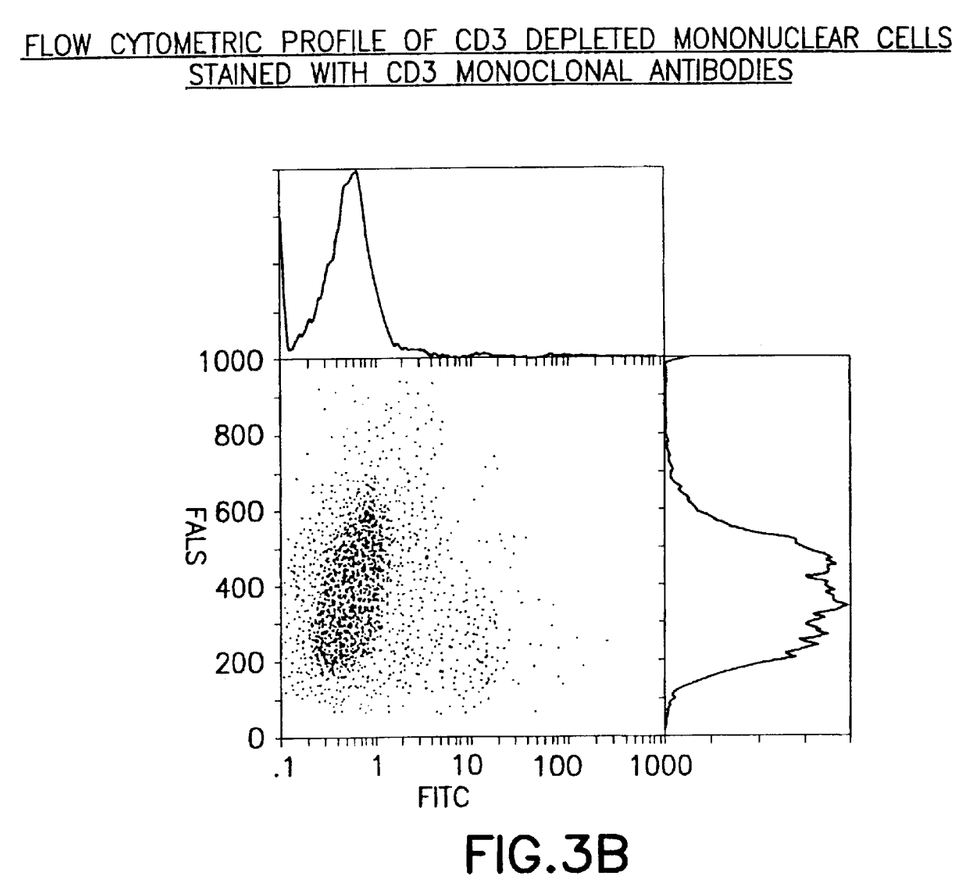
FIG. 3B shows the depletion of CD3+ cells from the isolated cell population.
Figure 3C:
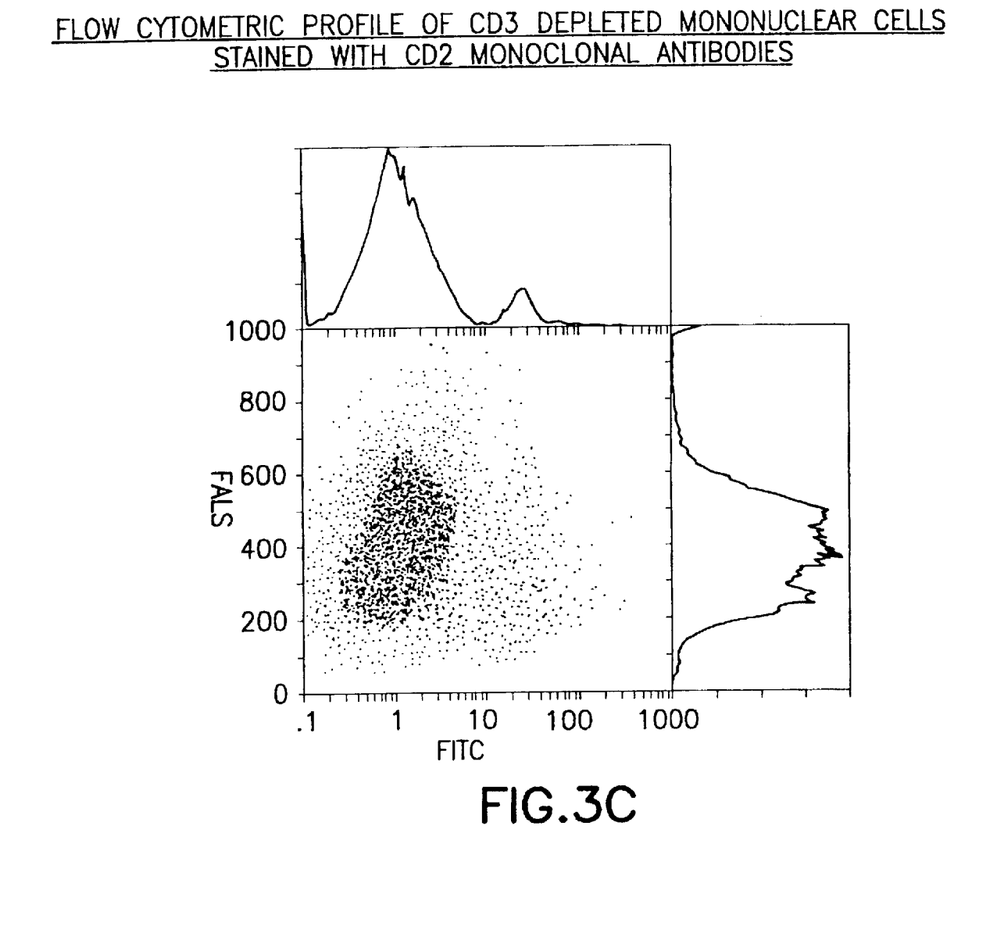
FIG. 3C shows that CD3 depleted cells having LDAP activity are CD2+.

FIG. 3 shows the flow cytometry analysis of the isolated cell populations. CD3 depleted cells were labelled with anti-CD3 antibody followed by a secondary FITC-conjugated antibody. As shown in FIG. 3B, CD3 depleted cell populations essentially showed no labelling for CD3, thus demonstrating the depletion of the CD3+ cells. The CD3 depleted cells were then labelled with anti-CD2 antibody followed by secondary FITC conjugated antibody. As shown in FIG. 3C, the CD3 depleted cells concomitantly expressed CD2, thus demonstrating the effecter cells with the highest levels of bactericidal activity to be CD3− and CD2+. FIG. 3A shows a negative control labelling with the secondary FITC, conjugate alone.

Bactericidal Activity Expressed in the Absence of Effector-target Cell Contact The bactericidal activity associated with the effector cells was assayed in the absence of effector cell-target cell contact to determine if the bacterial activity is facilitated through the release of a soluble factor. In this assay, effector cells were obtained as discussed above. To assay bactericidal activity, effector cells and bacterial cells were separated by a 0.4 μm mesh screen.

Alternatively, following 15 or 30 minute incubations with effector-bacterial cell contact the cell-free supernatants were collected, filtered, sterilized and incubated for an additional 15 or 30 minutes, respectively, with *S. aureus* target cells. The data in Table 3 demonstrate that the bactericidal activity is through a soluble secreted factor from the effector cells as no contact is needed between the effector cells and bacterial cells for bacterial killing to occur.

TABLE 3

BACTERICIDAL ACTIVITY EXPRESSED BY ISOLATED PERIPHERAL BLOOD LYMPHOCYTES IN THE ABSENCE OF EFFECTOR-TARGET CELL CONTACT

| | | No Effector-Target Cell Contact[1] | Cell-Free Culture Supernatants[2] |
|---|---|---|---|
| | | ---(% Killing)--- | |
| Incubation | | | |
| 15 min. | Spontaneous[3] | 12.4 | 3.3 ± 3.9 |
| | LAK[4] | 23.5 | 8.2 ± 3.9 |
| 30 min. | Spontaneous | 12.0 | 6.9 ± 3.9 |
| | LAK | 51.5 | 18.7 ± 3.9* |

[1]Effector and bacterial cells were separated by a .40 μm mesh screen during the incubation period.
[2]Following 15 and 30 min incubations with bacterial-effector cell contact, the supernatants were collected, filtered, sterilized, and incubated for an additional 15 or 30 minutes, respectively. Bactericidal activity is expressed as least square means ± standard error.
[3]Effector cells were incubated for 48 h in the absence of cytokine stimulation.
[4]Effector cells were incubated for 48 h with recombinant human interleukin-2.
*Significantly differ with respect to stimulation ($P < 0.05$).

Characterization of Lymphocyte-derived Antibacterial Protein (LDAP)

Activated lymphocyte cultures were subject to ammonium sulfate precipitation. The data of Table 4 demonstrates that the bactericidal activity partitioned with the 80% precipitated pellet of the supernatant from the activated cells.

TABLE 4

BACTERICIDAL ACTIVITY OF LYMPHOCYTE/S. aureus
CELL-FREE CULTURES FOLLOWING AMMONIUM SULFATE
PRECIPITATION

| Sample Fraction (Saturation) | Treatment | |
|---|---|---|
| | IL2 | Control |
| | ---(% Killing)--- | |
| Whole supernatant | 29.9 ± 2.3[a*] | 4.5 ± 2.3 |
| 80% precipitate pellet | 16.8 ± 2.3[b*] | 1.1 ± 2.3 |
| 80% supernatant | 0[c] | 0 |

[abc]Significantly different ($P \geq .01$) among the fractions within the IL2 treatment group.
*Significantly different ($P \geq .01$) between the IL2 and control cultures.
n = 4

It was further shown by the data of Tables 5 and 6 that the soluble protein responsible for the bactericidal activity could be heat inactivated by 30 minutes at 56° C. or with trypsin digestion at 37° C. for 24 hours at 1:50.

TABLE 5

THE EFFECT OF HEAT INACTIVATION ON THE ACTIVITY
OF BACTERICIDAL SUPERNATANTS

| Stimulation | Treatment[1] | Bactericidal Activity[2] -----(% Killing)---- |
|---|---|---|
| Spontaneous[3] | None | 12.7 ± 6.1 |
| | Heat | 10.0 ± 13.0 |
| Lymphokine activated[4] | None | 41.0 ± 6.1* |
| | Heat | 27.6 ± 6.1 |

[1]Cultures were incubated for 30 min at 56° C. (heat) or at room temperature (none).
[2]Following 30 min incubations with bacterial-effector cell contact, the supernatants were collected, filtered, sterilized, and incubated for an additional 30 minutes with bacterial targets. Bactericidal activity is expressed as least square means ± standard error.
[3]Effector cells were incubated for 48 h in the absence of cytokine stimulation.
[4]Effector cells were incubated for 48 h with recombinant human interleukin-2.
*Significantly differ with respect to treatment within a stimulation group ($P < 0.05$).

TABLE 6

THE EFFECTS OF TRYPSIN DIGEST ON ANTIBACTERIAL
ACTIVITY

| Treatment | Protein Concentration[1] (µg/ml) | Bactericidal Activity (% Killing) | Specific Activity (% Killing/µg) |
|---|---|---|---|
| Control[2] | 183 | 40% | .2 |
| Heated[3] | 183 | 26% | .14 |
| Trypsin[4] | 183 | 0 | 0 |

[1]Protein concentration from 80% ammonium sulfate precipitate.
[2]Cell free supernatants stored at 4° C. for 24 hours before incubation with S. aureus.
[3]Cell free supernatants stored at 37° C. for 24 hours before incubation with S. aureus.
[4]Cell free supernatant treated with trypsin (1:50) at 37° C. for 24 hours before incubation With S. aureus.

Spectrum of LDAP Against Pathogens of Food and Companion Animals

To test the spectrum of LDAP against different Gram-negative and Gram-positive pathogens, bacterial cultures were resuspended at $5 \times 10^4$ CFU/ml in HBSS and 50 ml of each strain was incubated with 450 µl of LDAP (129 µg/ml) for 30 minutes. Control tubes containing bacterial strains and HBSS only were run in parallel. After incubation, samples were plated onto blood agar and antibacterial activity was calculated as percentage of CFU of experimental tubes compared to controls.

The data of Table 7 demonstrates that LDAP has bactericidal activity against both gram negative and gram positive bacteria.

TABLE 7

SPECTRUM OF ANTIBACTERIAL ACTIVITY OF
LYMPHOCYTE-DERIVED ANTIBACTERIAL PROTEIN (LDAP)
AGAINST VARIOUS PATHOGENS

| Pathogen | Strain | Antibacterial Activity[1] |
|---|---|---|
| Staphylococcus aureus | Newbold 305 | 37% |
| Streptococcus uberis | MB21LR | 28% |
| Escherichia coli | 487 | 31% |

[1]Bacterial cultures were resuspended at $5 \times 10^4$ CFU/ml in HBSS and 50 ul of each strain was incubated with 450 ul of LDAP (129 µg/ml) for 30 min. Control tubes containing bacterial strains and HBSS only were run in parallel. After incubation, samples were plated onto blood agar and antibacterial activity was calculated as percentage CFU from experimental tubes compared to the controls.

Effects of Milk on Antibacterial Activity

Because of the importance of LDAP to the dairy industry with regard to bovine mastitis and other pathogen induced conditions which effect dairy cows, the effects of milk on the antimicrobial activity was assayed. Ammonium sulfate pellets were resuspended in either Tris-HCl or diluted with UHT milk to yield a final concentration of 91 µg/ml. As shown in Table 8, milk has no effects on the antimicrobial activity of LDAP making the protein suitable for the intramammary treatment of dairy cows.

TABLE 8

THE EFFECTS OF MILK ON ANTIBACTERIAL ACTIVITY

| Treatment | Protein Concentration[1] (µg/ml) | Bactericidal Activity (% Killing) | Specific Activity (% Killing/µg) |
|---|---|---|---|
| Tris-HCL[2] | 91 | 20% | .2 |
| Milk[3] | 91 | 18% | .2 |

[1]Protein concentration from 80% ammonium sulfate precipitate.
[2]Ammonium sulfate pellets were re-suspended in Tris-HCL to yield a final concentration of 91 µg.
[3]Ammonium sulfate precipitate was diluted with UHT milk to yield a final concentration of 91 µg.

Purification of LDAP

Mononuclear cells were isolated from the peripheral blood of healthy dairy cattle by centrifugation through Ficoll (1.077 g/ml). Monocytes were removed from the isolated mononuclear cells by adherence to plastic to obtain enriched lymphocytes. The lymphocytes ($2.5 \times 10^6$ cells/ml) were cultured for 48 hours with IL-2 (100 u/ml). Following culture, the cytokine activated lymphoid cells ($5 \times 10^5$ cells) were co-cultured with Staphyloccucus aureus ($5 \times 10^4$ cells) for 30 minutes. The cell-free culture supernatants were collected by centrifugation followed by filter sterilization to remove bacteria and effector cells.

Figure 1:
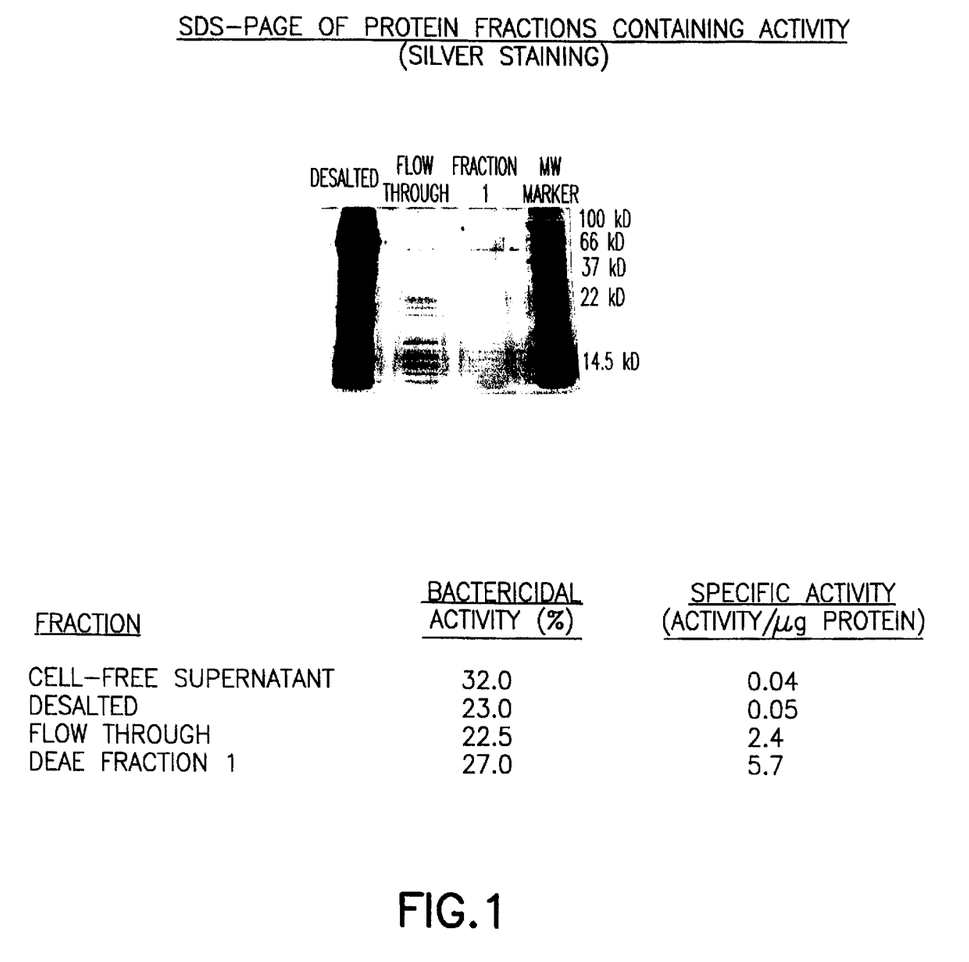
FIG. 1 shows the purification of LDAP with silver stained SDS-PAGE.
Figure 2:
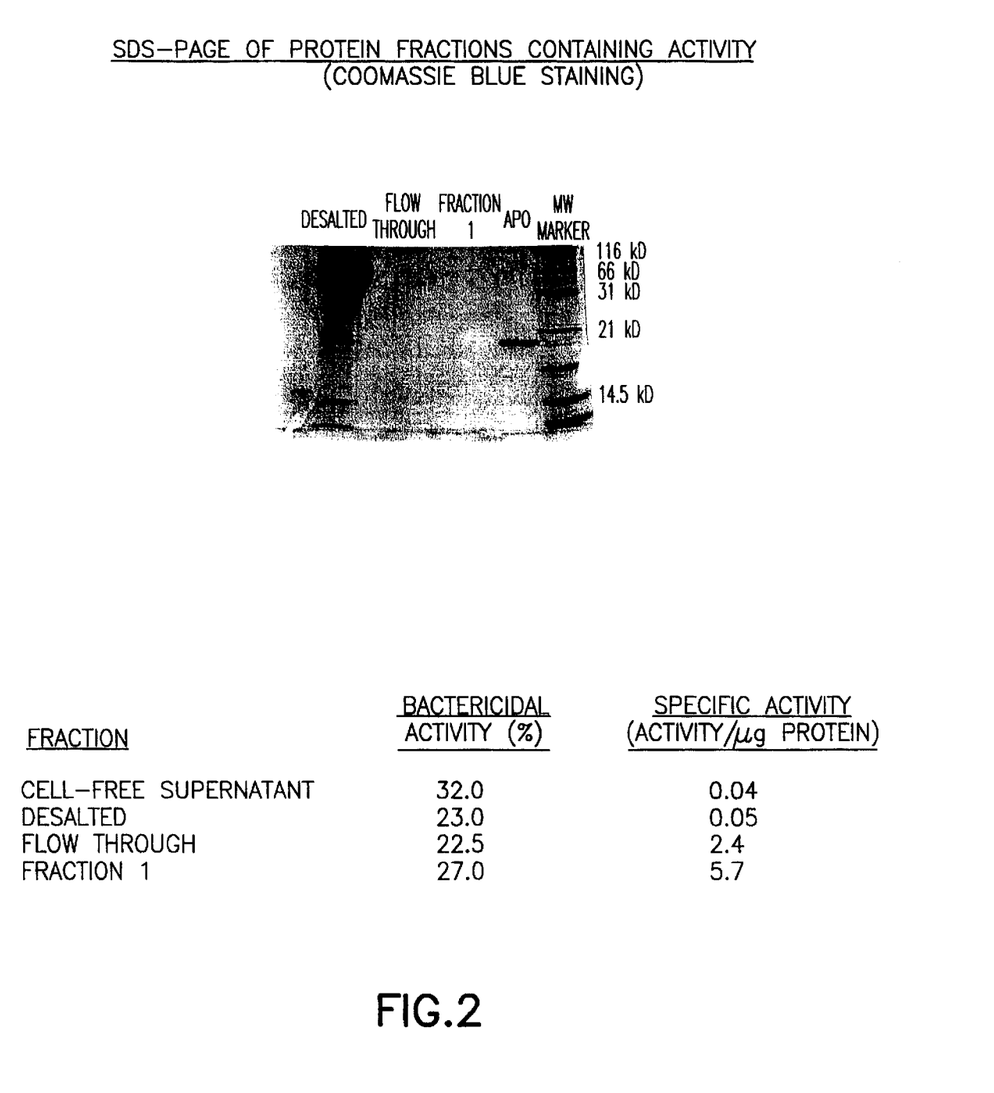
FIG. 2 shows the purification of LDAP with Coomassie Blue Stained SDS-PAGE.
Figure 4:
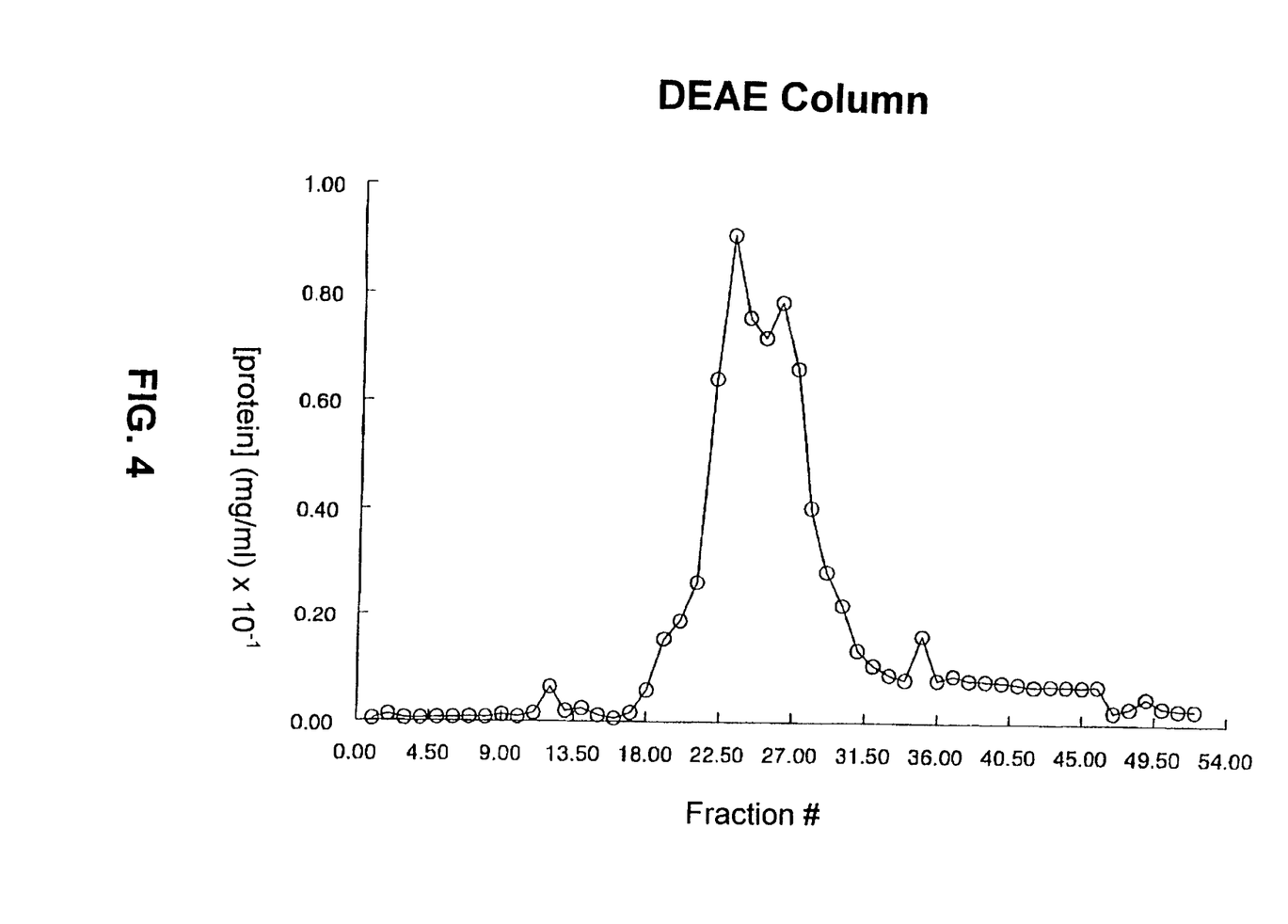
FIG. 4 shows the protein elution of LDAP from a DEAE column.

The cell-free supernatants were concentrated by ammonium sulfate precipitation (80%) and desalted on a BioRad 10 DG desalting column using the manufacturer's instructions. The de-salted preparation was loaded onto a DEAE column (DE52 Anion Exchanger, Whatman) and eluted using a linear salt gradient ranging from 0–0.5M NaCl in 20 mM Tris-HCl (pH 8.0). FIG. 4 shows the elution profile from the DEAE column. A total of four fractions were obtained and tested for antibacterial activity. The first fraction contained the antibacterial activity. In order to identify the putative protein, fraction 1 was subjected to SDS-PAGE using a 12.5% gel and the proteins were visualized using silver staining (FIG. 1) or Coomassie Blue Staining (FIG. 2).

Purification and identification of LDAP has been clearly demonstrated through the corresponding specific activity analysis of the purified protein. FIGS. 1 and 2 further show the specific activity (bactericidal activity/μg protein) associated with the cell-free supernatant, desalted ammonium sulfate precipitate, flow through of the DEAE column and fraction 1 of the DEAE column. As seen in FIGS. 1 and 2, the specific activity showed near a 150-fold increase (0.04 to 5.7) during purification, demonstrating the successful isolation of LDAP.

Most of the specific bacterial activity eluted with Fraction 1 from the DEAE column. Fraction 1 essentially contained two proteins, an approximately 65 kD protein which was identified as BSA and a 16 kD protein identified as LDAP.

What is claimed is:

1. A purified soluble lymphocyte-derived antimicrobial protein having the following properties:

a molecular weight of approximately 16 kD by SDS-PAGE, a susceptibility to inactivation by heat treatment at 56° C. for 30 minutes or by trypsin, expression by CD3−, CD2+ cytokine stimulated cells, and antibacterial activity against both Gram-negative and Gram-positive bacteria, including *Staphylococcus aureus*.

2. The protein of claim 1 wherein said antimicrobial activity is against pathogens of food and companion animals.

3. The protein of claim 1 which further has antimicrobial activity against *Streptococcus uberis* or *E. coli*.

4. The protein of claim 1 wherein said protein is purified from cytokine and bacteria activated lymphocytes.

5. The protein of claim 4 wherein said cytokine is IL-2.

6. A method for killing bacteria comprising topically exposing bacteria to an effective amount of the protein of claim 1.

7. The method of claim 6 wherein the exposure of the bacteria is in vitro.

8. A protein produced by:

(a) isolating lymphocytes from bovine mammary gland tissue or bovine peripheral blood, (b) activating the isolated lymphocytes with interleuken-2, (c) culturing the activated lymphocytes with *Staphylococcus aureus*, (d) obtaining a cell-free supernatant from said culture, (e) precipitating the cell-free supernatant with ammonium sulfate (f) desalting the precipitated cell-free supernatant, and (g) eluting the desalted precipitated cell-free supernatant on an ion exchange column using a linear salt gradient to obtain a fraction containing the protein.

9. The protein of claim 8 which has antimicrobial activity against both gram positive and gram negative bacteria.

10. The protein of claim 9 wherein the gram positive bacteria include *Staphylococcus aureus*.

11. A method for the treatment or prophylaxis of mastitis in food or companion animals comprising administering by teat dip to the teat of said animal an effective amount of the protein of claim 1.

12. The method of claim 11 wherein said animals are cattle.

13. A method for the treatment or prophylaxis of mastitis in food or companion animals comprising intramammary administration to the teat of said animal an effective amount of the protein of claim 1.

14. The protein of claim 1 which comprises a chemical, fluorescent, or radioactive marker.

* * * * *